US005569208A

United States Patent [19]
Woelpper et al.

[11] Patent Number: 5,569,208
[45] Date of Patent: Oct. 29, 1996

[54] SYSTEM FOR MANAGING DELIVERY OF CONTRAST MEDIA

[75] Inventors: William R. Woelpper, Sandy; Richard L. Young, Alpine; Ronald L. Stoker, South Jordan, all of Utah

[73] Assignee: Merit Medical Systems, Inc., South Jordan, Utah

[21] Appl. No.: 509,926

[22] Filed: Aug. 1, 1995

[51] Int. Cl.⁶ ................................................ A61M 5/178
[52] U.S. Cl. ............................ 604/183; 604/83; 604/251
[58] Field of Search ................................. 604/251, 254, 604/258, 183, 246, 248, 83; 251/98, 111, 101; 137/587, 589

[56] References Cited

U.S. PATENT DOCUMENTS

| | | |
|---|---|---|
| 4,553,964 | 11/1985 | Sasaki ........................................ 604/248 |
| 4,673,397 | 6/1987 | Lynn et al. ................................ 604/251 |
| 4,734,091 | 3/1988 | Boyle et al. . |
| 5,328,463 | 7/1994 | Bartone et al. . |
| 5,356,375 | 10/1994 | Higley . |
| 5,423,346 | 6/1995 | Daoud ....................................... 137/399 |
| 5,423,751 | 6/1995 | Harrison et al. ........................... 604/83 |
| 5,443,453 | 8/1995 | Walker et al. ............................ 604/248 |

Primary Examiner—Randall L. Green
Assistant Examiner—V. Alexander
Attorney, Agent, or Firm—Workman Nydegger Seeley

[57] ABSTRACT

A system for managing delivery of contrast media from a contrast media source to a patient. The system includes a chamber for receiving fluid from the contrast media source in a controlled manner. Attached at one end of the chamber is an inlet line and, at the opposite end, an outlet line. Disposed in the outlet line is a valve. The valve provides a first position which permits the flow of contrast media through the line. The valve further provides a second position which permits flow of fluid from the point of the valve toward the patient, while at the same time venting the system at the point of the valve.

21 Claims, 8 Drawing Sheets

5,569,208

SYSTEM FOR MANAGING DELIVERY OF CONTRAST MEDIA

BACKGROUND OF THE INVENTION

1. The Field of the Invention

This invention relates to a system for managing deliver of parenteral fluids and, more particularly, to a system for managing deliver of contrast media.

2. The Relevant Technology

Contrast media is widely used in a variety of medical procedures typically involving catheterization. In such procedures, the catheter serves to deliver the contrast media to canals, vessels, passage-ways or other body cavities. Contrast media may also be used in association with dilatation catheters in which case the contrast media is contained within the catheter rather than being delivered into the patient. Contrast media may also be injected in other fashions. Regardless of the means of deliver, the contrast media serves the same function in each procedure. Specifically, the contrast media serves to provide a substance which can be viewed by medical personnel rising monitoring apparatus used in conjunction with the particular procedure. For example, contrast media can allow medical personnel to view a variety of different conditions, or lack thereof, on x-ray equipment.

A concern common to all procedures utilizing contrast media is the high cost of the contrast media itself. It is a relatively rare occasion for a procedure to use an exact number of bottles or bags of contrast media. More often, a procedure will leave some portion of a bag or bottle remaining. In addition, contrast media may be left in the reservoir and tubing of a contrast media deliver system. Although the amount of contrast media which is wasted in a single procedure is relatively small, a medical facility which performs these procedures routinely will end up disposing a substantial amount of unused contrast media. Procedures and apparatus for minimizing the amount of contrast media which is wasted in a medical procedure are, therefore, highly desirable.

Methods for reducing the amount of contrast media wasted in a medical procedure would need to allow use of the remaining bottle or bag of contrast media on a subsequent patient and to eliminate contrast media remaining in the reservoir or tubing at the end of a procedure. The use of the contrast media remaining in the bag or bottle at the end of the procedure requires assurances that the contrast media has not been contaminated in some way by the original patient.

A number of systems for controlling contrast media to be delivered to a patient have been developed. These systems commonly will incorporate features designed to minimize the amount of contrast media which is wasted. A typical prior art system is shown in FIG. 1 of the appended drawings. FIG. 1 depicts a prior art contrast media control system, designated generally as 10, as it would be used in angiography and angiplasty procedures, hereinafter "angio procedures."

As depicted, such a system will typically include a contrast media source shown here as contrast media bag 12 but also available as a bottle (not shown). Contrast media bag 12 hangs on I.V. pole 14 and is contained integrally in cuff assembly 16 which acts as a pressurizer when hand pump 18 is used to inflate cuff 20. Pump valve 22 allows for inflation and deflation of cuff 20. When hand pump 18 is squeezed it acts to inflate cuff 20 and applies pressure to contrast media bag 12.

Contrast media bag 12 is accessed via bag connection assembly 24 to which inlet line 26 is connected. Two position inlet valve 28 is disposed in inlet line 26. Inlet valve 28 can be turned "on" by placing the fins of the valve in line with inlet line 26 as shown. In this position, fluid can flow from contrast media bag 12 through inlet line 26 to reservoir 30. Inlet valve 28 can, alternatively, be turned "off" by placing the fins of the valve perpendicular to inlet line 26 (not shown). In this position, inlet line 26 is closed and does not allow flow of contrast media from contrast media bag 12 through inlet line 26 into reservoir 30.

Upper one way valve 32 and lower one way valve 34 are also disposed in inlet line 26. These valves provide a redundant system for preventing contamination of the contrast media contained in contrast media bag 12 by preventing any fluid movement toward contrast media bag 12 from the point of the valve. Although a single one way valve would theoretically be sufficient, a dual one way valve system is used to ensure contamination is prevented. In this way, any contrast media remaining in contrast media bag 12 at the end of a procedure can be used for another procedure.

Reservoir 30 has a cap 36. Cap 36 has a inlet line connection 38 and a reservoir vent 40 disposed thereon. Contrast media flowing from contrast media bag 12 into reservoir 30 flows directly out of inlet line 26 and would, without intervention, fall to the bottom or fluid level of reservoir 30. The act of falling and splashing on the bottom of reservoir 30 or into the fluid in reservoir 30 can have the undesirable effect of causing micro bubbles in the contrast media. Micro bubbles injected into a patient can have serious side effects particularly in a system such as this where fluid may be fed directly into the heart. If a micro bubble were to lodge in the myocardia of the heart, it could stop the flow of blood and result in the death of that portion of the heart tissue. For such reasons, a deflector assembly (not shown) is typically employed to force fluid entering reservoir 30 to flow down the sides of reservoir 30.

Reservoir vent 40 allows contrast media to flow into reservoir 30 initially. Because the system is closed, even with inlet valve 28 in the "on" position, contrast media will not flow from contrast media bag 12 into reservoir 30. The system must be vented before the contrast media can flow to reservoir 30. This is accomplished by pushing on cap 42 which is disposed on reservoir vent 40. Cap 42 has a small slit cut therein which opens slightly when pressure is applied. When the desired level of fluid is reached in reservoir 30, the medical user releases cap 42 which allows the slit to close. With the cap back in place, contrast media will cease to flow to the reservoir and will only resume flowing if cap 42 is removed or some contrast media is removed from the reservoir.

Fluid flows out of reservoir 30 through outlet line 46. Ball valve 44 floats on any contrast media contained within reservoir 30. Ball valve 44 is designed to close off reservoir 30 when there is no contrast media remaining in reservoir 30. Unfortunately, these valves often leak to some degree often due to slight circumferential differences between ball valve 44 and outlet 48.

Contrast media flows through outlet line 46 to fluids administration system designated generally at 50. Fluids administration set 50 includes a syringe 52 which is connected to a catheter manifold 54 with a connection assembly 56. Syringe 52 includes a barrel 58 and a plunger 60.

Manifold fluid line 62 is defined by catheter manifold 54. Manifold fluid line 62 provides for movement of a variety of pressurized fluids through catheter manifold 54. Fluid flow is controlled by a number of manifold valves which are disposed in manifold fluid line 62. The flow of contrast media is controlled by contrast media manifold valve 64 which incorporates tab 66. Other typical manifold valves are represented by saline manifold valve 68 which incorporates tab 70 and pressure manifold valve 72 which incorporates tab 74. Each valve is associated with a fluid line. Contrast media manifold valve 64 is associated with outlet line 46. Saline manifold valve 68 is associated with saline line 76. Pressure manifold valve 72 is associated with pressure line 78.

Each fluid line is connected to catheter manifold 54. Outlet line 46 is connected via a contrast media connection assembly 80. Saline line is connected via a saline connection assembly 82. Pressure line 78 is connected via pressure connection assembly 84.

The operation of each manifold valve is identical. To stop a fluid from passing through the valve, the valve is turned so that the tab points toward the fluid line. In this position, the valve occludes the fluid line at which the tab is pointing. At the same time, the valve permits fluid to flow through the manifold fluid line 62. In FIG. 1, the tabs of all of the valves are pointing toward each respective line. This indicates that fluid is being allowed to pass through manifold fluid line 62. Concurrently, outlet line 46, saline line 76, and pressure line 78 are being occluded.

Opposite syringe 52 on catheter manifold 54 is a catheter connection assembly 86. A catheter (not shown) would be connected to catheter connection assembly 86 and would, thus, be connected to catheter manifold 54. During an angio procedure, various fluids would pass through catheter manifold 54 to a catheter (not shown) and then intracorporeally to a patient.

Focusing now on the administration of contrast media to a patient, the contrast media manifold valve 64 must be turned so that tab 66 is pointed toward syringe catheter connection assembly 86 in order for contrast media to be drawn into barrel 58 of syringe 52. When syringe 52 is filled to the desired level, the contrast media is then injected into the patient. The act of filling syringe 52 to the desired level and injecting the contrast media into the patient is commonly referred to as administering a bolus of contrast media.

As contrast media is drawn into syringe 52, reservoir 30 begins refilling to the level held prior to the drawing of contrast media into syringe. This occurs because the system is closed and the drawing of contrast media into syringe 52 creates a pressure differential which causes contrast media to flow into the reservoir. This pressure differential exist until reservoir 30 is refilled to its previous level.

As previously discussed, contrast media is expensive. When the medical professional is approaching completion of a procedure, therefore, he or she will turn off the supply of contrast media by placing inlet valve 28 in the "off" position. In this position, inlet valve 28 occludes inlet line 26 and prevents contrast media from flowing into reservoir 30. When this is done, the medical professional has effectively two boluses left. One bolus comes from the contrast media contained within the length of tubing comprising outlet line 46 and the second bolus from the contrast media contained within the reservoir.

When filling syringe 52 for these last two boluses the medical professional must work against the closed system. Filling syringe 52 for the second to last bolus results in substantially draining the reservoir into outlet line 46. This creates a vacuum effect in reservoir 30 which pulls against the action of syringe 52.

The vacuum effect is particularly strong when pulling the remaining fluid from outlet line 46 for the last bolus. The force is so strong in fact, that although plunger 60 of syringe 52 typically can be pulled back with sufficient force, nevertheless fluid does not flow into fill barrel 58 of syringe 52 for the last bolus. In order to overcome this vacuum effect, the medical professionally must overcome the seal of ball valve 44 and open vent 40 in reservoir 30, although it may be possible to dislodge ball valve 44 simply by flicking reservoir 30 with a finger.

More often ball valve 44 gets lodged and more elaborate steps must be taken. In order to dislodge ball valve 44, vigorous shaking or tapping of reservoir 30 may sometimes be required. Reservoir 30 may even need to be turned upside down to dislodge ball valve 44 As will be appreciated, this is less than desirable in the midst of a delicate medical procedure Once ball valve 44 is dislodged the system can be vented to atmosphere by pushing on vent cap 42 to allow the system to vent through vent 40. Syringe 52 can then be filled with contrast media from outlet line 46 for administration of the last bolus.

A problem in the art of contrast media control systems is the creation of microbubbles from the contrast media falling into reservoir 30. Several additional problems are particularly apparent during the last two boluses of a procedure. Leaking around ball valve 44 is undesirable. The tendency for ball valve 44 to get lodged and require significant manipulation to dislodge is distracting at best. Applying pressure to vent cap 42 and dislodging of ball valve 44 in order to vent the system and to allow the last shots to flow easily from the reservoir and outlet line adds complexity to a procedure that is already delicate.

SUMMARY AND OBJECTS OF THE INVENTION

In order to solve the problems known in the art, as stated above, it is an object of the present invention to provide a system for managing delivery of contrast media or other fluids which is self venting.

It is an additional object of the present invention to provide for self venting through utilization of a valve assembly having a position which allows the system to be vented to atmosphere.

A further object of the present invention is to provide a system which greatly reduces or eliminates the creation of microbubbles in the contrast media as it fills the reservoir.

Additional objects and advantages of the present invention will be set forth in the description which follows, and in pan will be obvious from the description, or may be learned by the practice of the invention. The objects and advantages of the invention may be realized and obtained by means of the instruments and combinations particularly pointed out in the appended claims.

To achieve the foregoing objects, and in accordance with the present invention as embodied and broadly described herein, there is provided an inventive system tier managing delivery of contrast media from a contrast media source to a patient.

The contrast media control system includes a chamber means for receiving fluid from a contrast media source in a controlled manner to which is attached at one end an inlet line and, at the opposite end, an outlet line. Disposed in at least one of the inlet line and outlet line is a valve means.

The valve means provides a first position which permits the flow of contrast media through the line. The valve means further provides a second position which permits flow of fluid from the point of the valve means toward the patient, while at the same time venting the system at the point of the valve means.

The above stated objects and features of the present invention, as well as other objects and features of the present invention, will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawing depict only a typical embodiment of the invention and are not therefore to be considered to be limiting of its scope, the invention will be described and explained with additional specificity and detail through the use of the accompanying drawings in which:

FIG. 5 shows an initial fill of the chamber means.

FIG. 6 shows the chamber means filling to maintain the preset level.

FIG. 7 shows the chamber means being pulled empty by the action of the syringe during the second to last shot.

FIG. 8 shows chamber means empty and the outlet line, shown in cross section, supplying the contrast media for the last shot.

DETAILED DESCRIPTION OF THE PREFERRED EMBODIMENTS

Reference is now made to the embodiment illustrated in FIGS. 2 through 8 wherein like numerals are used to designate like parts throughout. Although the system description will focus on the control of contrast media, it will be understood and appreciated that such a system could be used in conjunction with any fluid.

Figure 1:
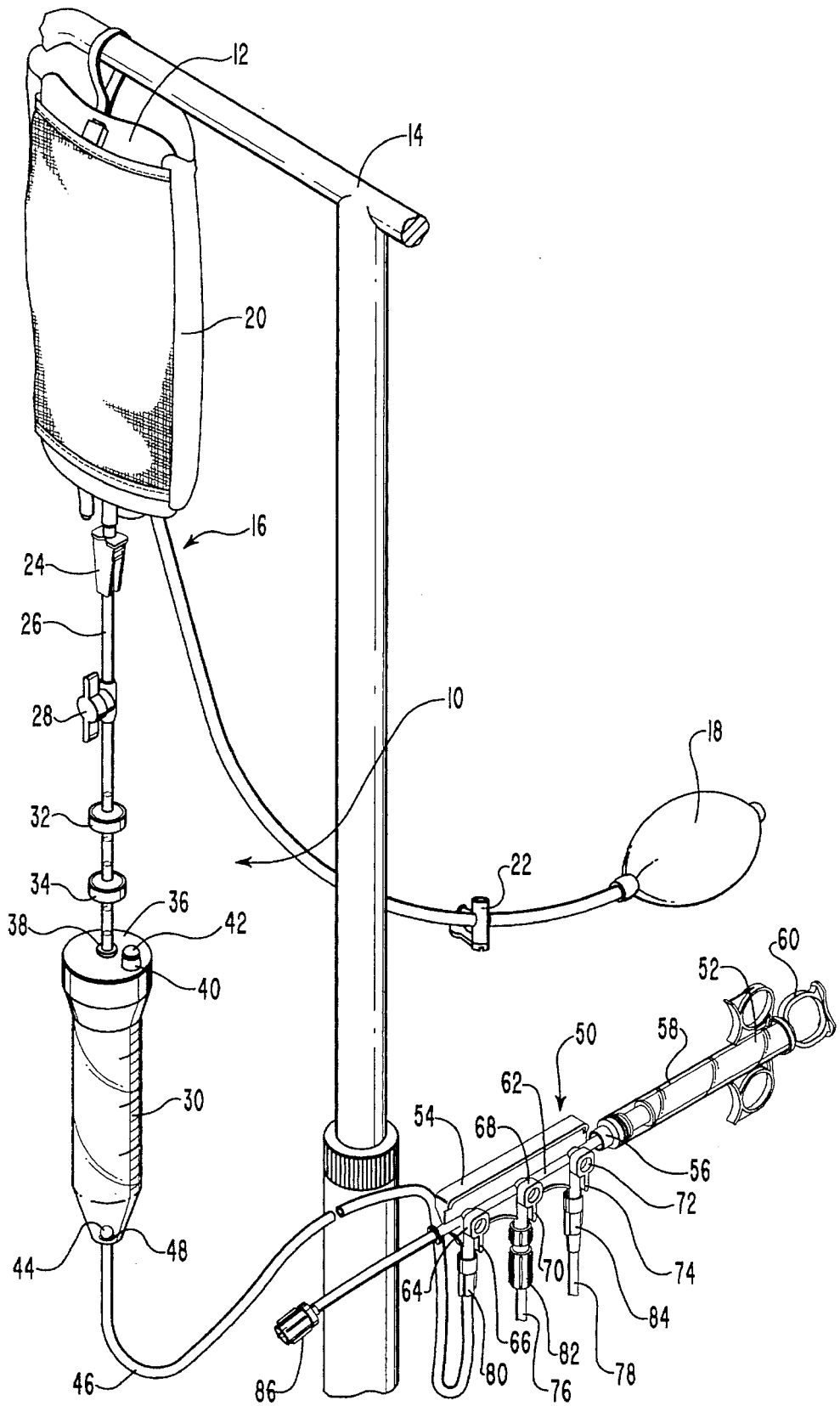
FIG. 1 is a perspective view of a typical prior art system as it would be used in a typical application.
Figure 2:
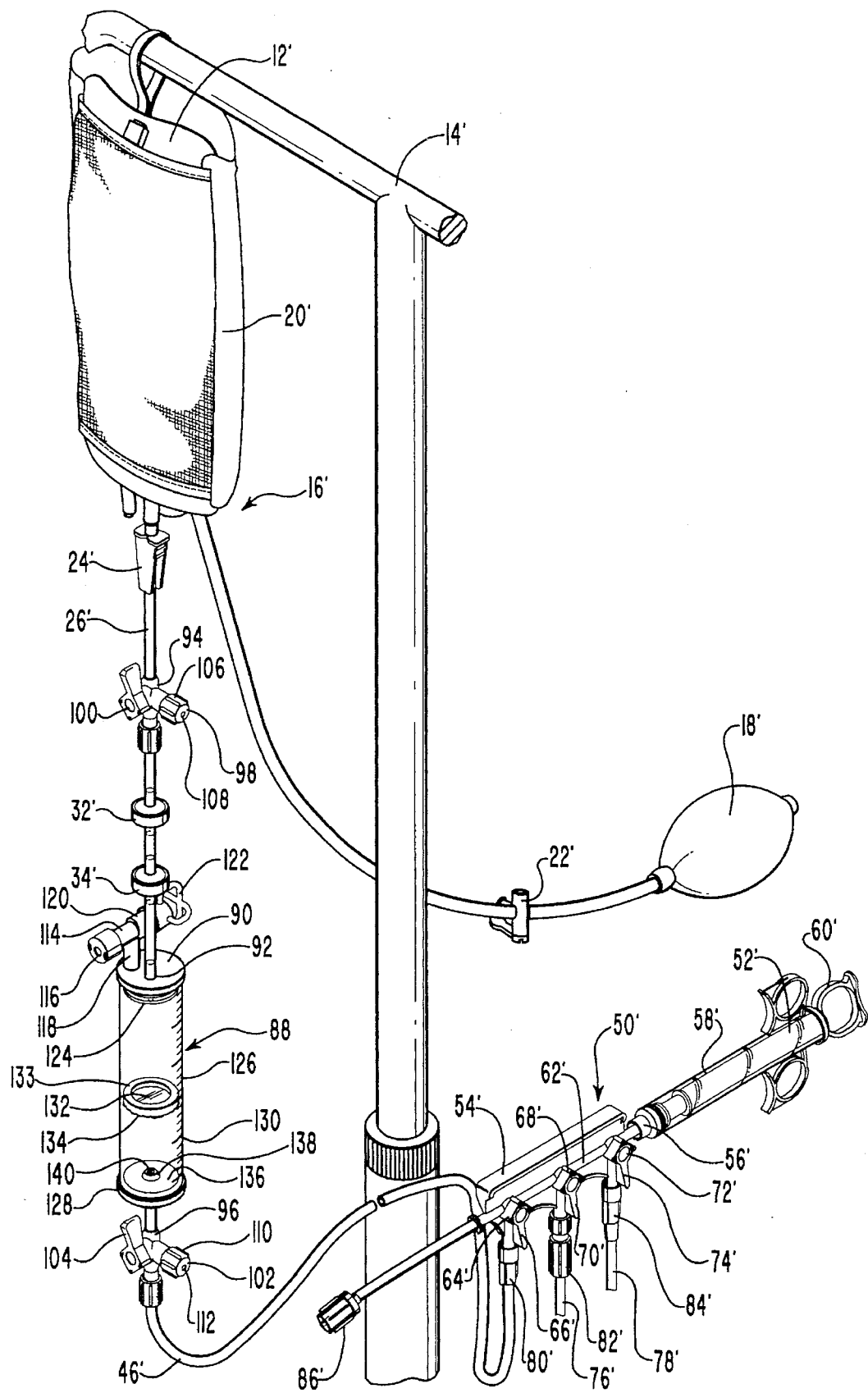
FIG. 2 is a perspective view of the inventive contrast media delivery system as it would be used in a typical application.

FIG. 2 shows a currently preferred embodiment of the inventive system for managing delivery of contrast media as it would be used for angio procedures. As will be seen, the general environment depicted is the same as that depicted in FIG. 1. The contrast media bag 12, cuff assembly 16, inlet line 26, outlet line 46, and fluids administration set 50 as described above in association with FIG. 1 are all represented in FIG. 2 as well.

In FIG. 2, contrast media bag 12 is attached to a chamber means 88 via inlet line 26'. Inlet line 26' attaches to a inlet housing 90 via inlet port 92. A series of valves are disposed in inlet line 26' as described below.

FIG. 2 incorporates inlet valve means 94 disposed in inlet line 26'. Outlet valve means 96 is disposed in outlet line 46'. Each of these valves means functions identically. Each valve incorporates a self vent which vents the system to atmosphere at the point of the valve. Inlet valve means 94 has associated therewith a self vent 98 and a handle 100. Outlet valve means 94 has associated therewith a self vent 102 and a handle 104.

Each valve means further provides a first position which permits flow of fluid through the line without venting to atmosphere. In this position, see, e.g., FIG. 5, handle 100 of inlet valve means 94 points toward inlet self vent 98. Each valve means also provides a second position which permits fluid flow from the position of the valve means toward the patient while at the same time venting the system to atmosphere. In this second position, inlet handle 100 of inlet valve means 94 points upward which would be toward contrast media bag 12' as depicted in FIG. 2. Outlet valve means 96 works in the same manner.

Inlet self vent 98 includes an inlet vent housing 106 and an inlet vent port 108. Outlet self vent 102 includes an outlet vent housing 110 and outlet vent port 112. When inlet handle 100 is in proper position, air can flow through inlet vent port 108 and into the system. Outlet vent port 112 works in the same manner.

Also disposed in inlet line 26' are upper one way valve 32' and lower one way valve 34'. These one way valves function, as described above in regard to FIG. 1, to keep the contrast media remaining in contrast media bag 12' from being contaminated Also depicted in FIG. 2 is chamber vent 114. Chamber vent 114 comprises a push button 116, a chimney 118, a filter housing 120, and a protective cage 122. Chamber vent 114 is disposed on inlet housing 90 of chamber means 88.

Push button 116 can be employed to vent chamber means 88 to atmosphere. When push button 116 is pushed in, chamber means 88 is vented to atmosphere. Push button 116 can function in a variety of ways. For example, push button 116 may be designed such that it springs out to a non-vent position when released. Alternatively, push button 116 may be designed to stay pushed in, and thus allow venting. In this instance, push button 116 would need to be further depressed by the medical professional in order to release and spring back into a non-vent position. It will be appreciated that push button 116 can have numerous configurations without departing from the essence of the present invention.

Attached to inlet housing 90 on the internal side is deflector 124. Deflector 124 acts to channel fluid entering chamber means 88 down the sides or barrel 126 of chamber means 88 rather than allowing the fluid to fall onto outlet housing 128 or into any fluid which might be present in chamber means 88. By channeling fluid down chamber barrel 126, the introduction of microbubbles into the fluid is greatly reduced or eliminated.

Gradation markings 130 on chamber barrel 126 are also shown. Markings 130 allow the medical professional to fill chamber barrel 126 to a desired level. Markings 130 will typically represent volume in cubic centimeters. Chamber barrel 126 is preferably constructed of a clear medical grade plastic so that the fluid level is easily ascertainable.

A membrane 132 is disposed within chamber barrel 126. Membrane 132 is preferably made of silicone or latex but other materials may be employed. Membrane 132 is surrounded by membrane ring 133 which is manufactured of a medical grade plastic material. Membrane 132 floats on top of any fluid 134 contained within chamber barrel 126. In FIG. 2, the fluid level is shown as somewhat less than half full with membrane 132 floating on the surface. As the fluid recedes from chamber barrel 126, membrane 132 moves toward the bottom of chamber barrel 126. When membrane 132 reaches the floor 136 of outlet housing 128, membrane 132 engages a nipple 138 and forms a tight seal.

Figure 3:
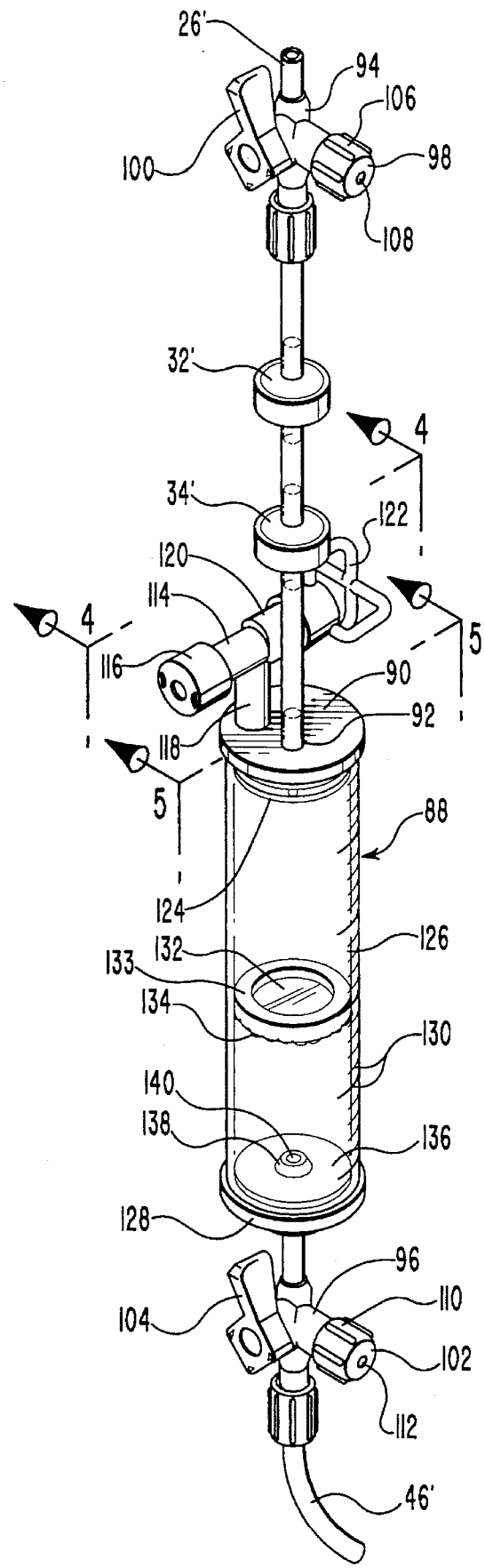
FIG. 3 is perspective view of the chamber means of the system for managing delivery of contrast media to a patient and associated valves and tubing.

Nipple 138 can best be seen in FIG. 3. Nipple 138 surrounds the interior opening of outlet port 140 in outlet housing 128. When membrane 132 reaches floor 136, membrane 132 sealing engages nipple 138 and occludes outlet port 140. A strong seal is formed by the interaction of membrane 132 and nipple 138.

Cage 122 is also better seen in FIG. 3. When pushing push button 116 to allow for venting to atmosphere, a medical professional is tempted to place the forefinger over the end of filter housing 120 and to push push button 116 with the thumb. This results in the forefinger of the medical professional occluding the vent passageway and venting to atmosphere is prevented. Cage 122 prevents the medical professional from occluding the vent passageway in this manner.

Figure 4:
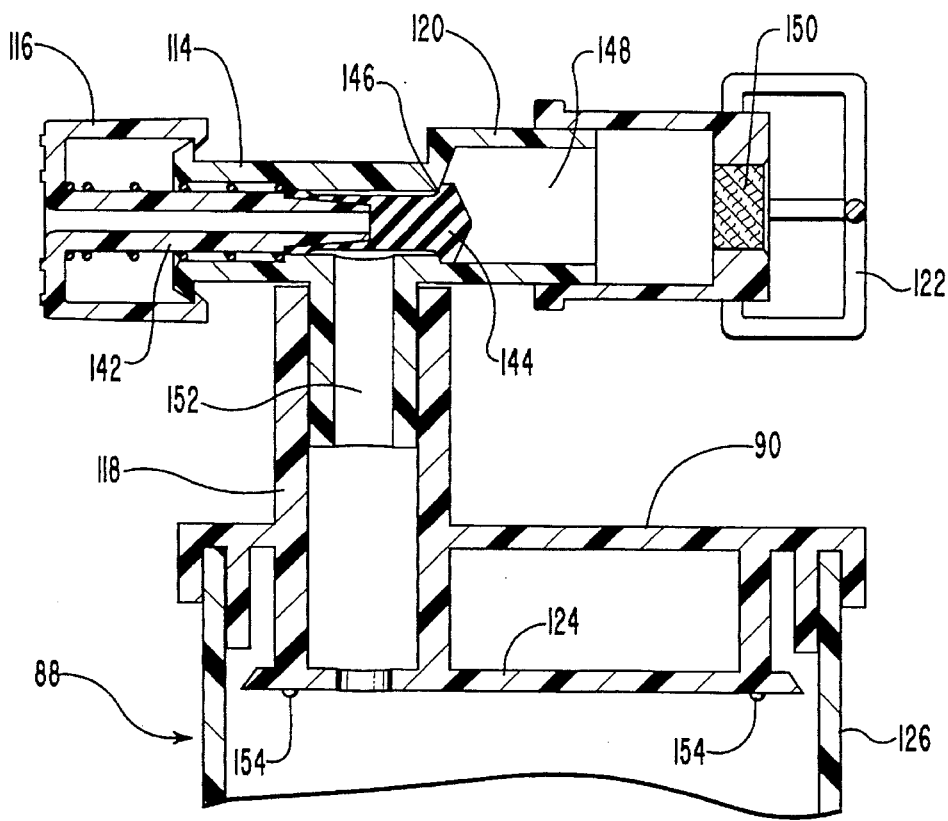
FIG. 4 is a cross sectional view of the chamber vent along lines 4—4 of FIG. 3 showing the push button in the released position.
Figure 4A:
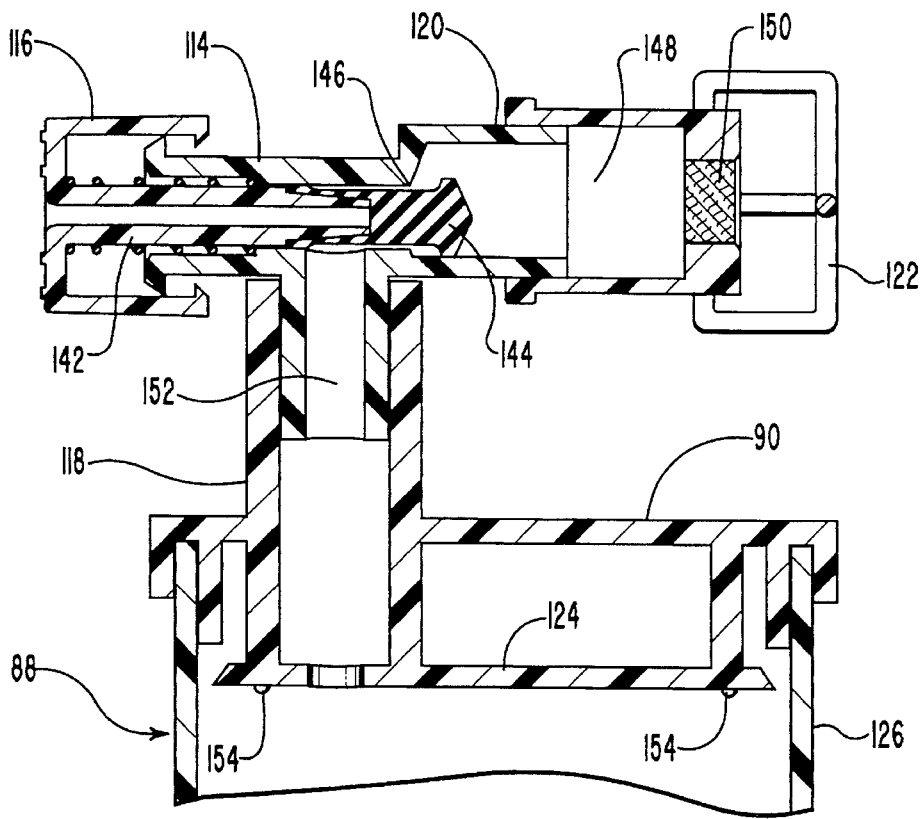
FIG. 4A is a cross sectional view of the chamber vent along lines 4—4 of FIG. 3 showing the push button in the depressed position.

Turning to FIGS. 4 and 4A, a cross sectional view of chamber vent 114 illustrates the internal configuration of chamber vent 114. Push button 116 is disposed at one end of rod 142 and, at the opposite end of rod 142, is seal member 144. Seal member 144 and lip 146 are tapered so as to conform to one another and provide a strong seal. In FIG. 4, push button 116 is in a first or "out" position such that seal member 144 engages lip 146 of vent passageway 148 to form a seal that prevents passage of air through passageway 148. Integral to passageway 148 is filter 150. Filter 150 is typically a microfilter designed to allow air to flow through filter 150 while at the same time filtering out a variety of airborne impurities.

FIG. 4A shows push button 116 in a second or "in" position. In this position, seal member 144 is urged away from lip 146 and air can flow around seal member 144 and rod 142 through interface tube 152. As can be seen in both FIGS. 4 and 4A, interface tube 152 is contained substantially within the top portion of chimney 118. Interface tube 152 is shown bonded into chimney 118.

Chimney 118 extends through inlet housing 90 and through deflector 124. If chimney 118 were to extend only through inlet housing 90, splashback from fluid falling onto deflector 124 could clog chimney 118. This potential clogging problem is avoided by routing chimney 118 through deflector 124.

Also visible in FIGS. 4 and 4A are detents 154. These prevent membrane 132 from becoming lodged against deflector 124. In some instances, a medical professional will determine that the shot that has been drawn into syringe 52' is not needed. When this occurs, the medical user will eject the contrast media contained in syringe 52' back into outlet line 46' which forces the contrast media currently in outlet line 46' into chamber means 88. Membrane 132, floating on top of the contrast media in chamber means 88 is carried to the top of chamber barrel 126. By incorporating detents 154 disposed on deflector 124, the tendency for membrane 132 to sealingly engage deflector 124 is greatly reduced or eliminated.

Figure 5:
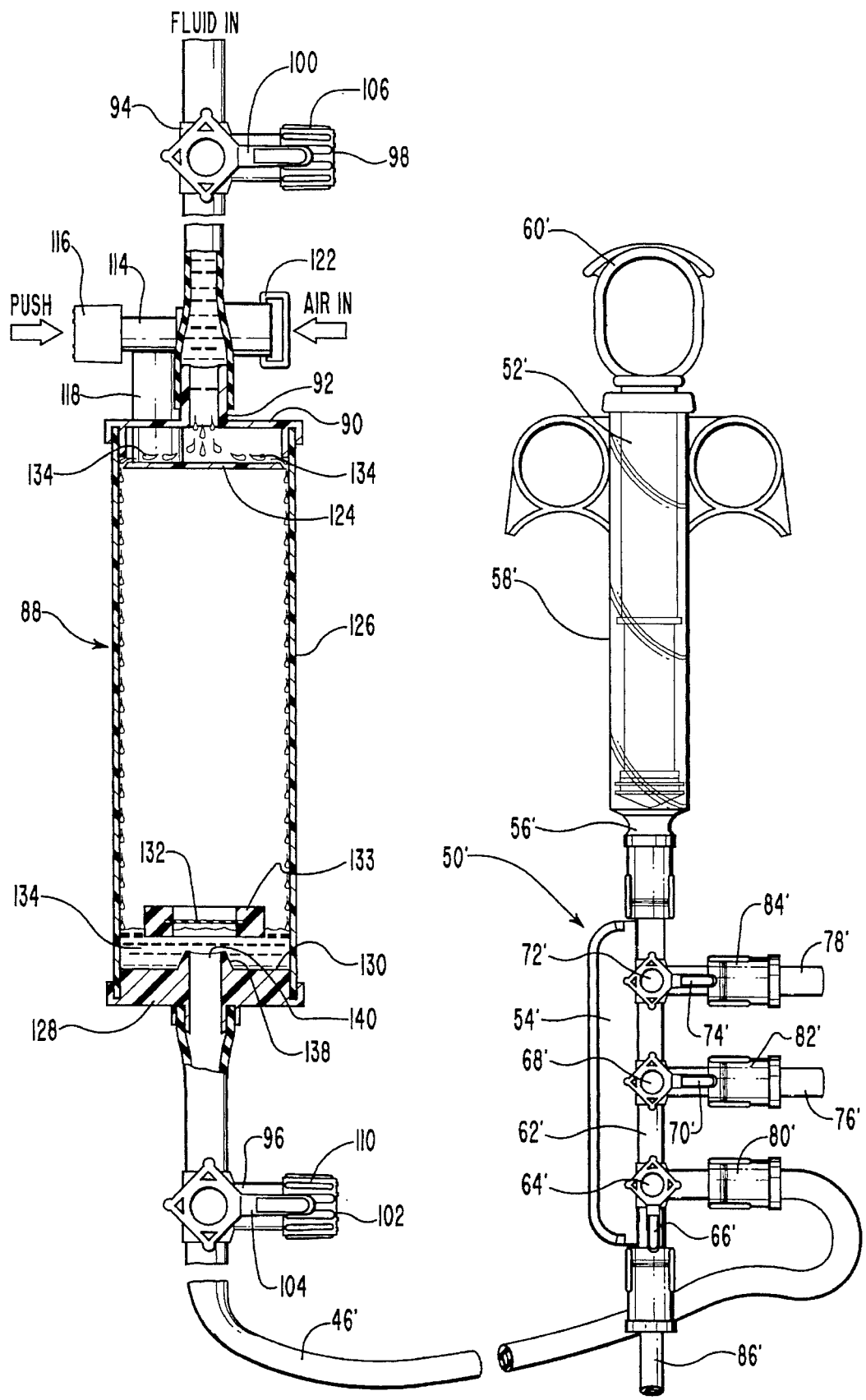
FIGS. 5 through 8 are cross sectional views along lines 5—5 of FIG. 3 showing various stages of the inventive system in use, the chamber means is shown in cross section in each.

FIGS. 5 through 8 show the inventive system in different stages of use, with chamber means 88, inlet port 92, and outlet port 140 shown in cross section. FIG. 5 shows an initial fill of chamber barrel 126. Inlet handle 100 of inlet valve means 94 is turned toward inlet self vent 98 indicating that contrast media can flow therethrough. Push button 116 is pushed in allowing the system to vent to atmosphere and permitting contrast media to flow into chamber means 88.

Contrast media flows through inlet line 26 into inlet port 92 and onto deflector 124 where it is routed down the sides of chamber barrel 126. As chamber barrel 126 fills, membrane 132 rises.

Outlet handle 104 of outlet valve means 96 is turned toward outlet self vent 102 indicating that outlet line 46' is open rather than occluded. Fluid will not flow through outlet line 46' during the initial fill, however, because outlet line 46' will be filled with air. Tab 66' of contrast media manifold valve 64' is shown pointing toward outlet line 46' indicating that outlet line 46' is occluded at that point.

To remove this air and draw fluid into outlet line 46', a medical professional will place tab 66' of contrast media manifold valve 64' so that it points toward syringe 52. The medical professional will then retract plunger 60' of syringe 52' until a small amount of contrast media is pulled into barrel 58' of syringe 52'. This contrast media and air is expelled into a waste receptacle (not shown). At this point the system is debubbled and ready for administration of contrast media to a patient.

Figure 6:
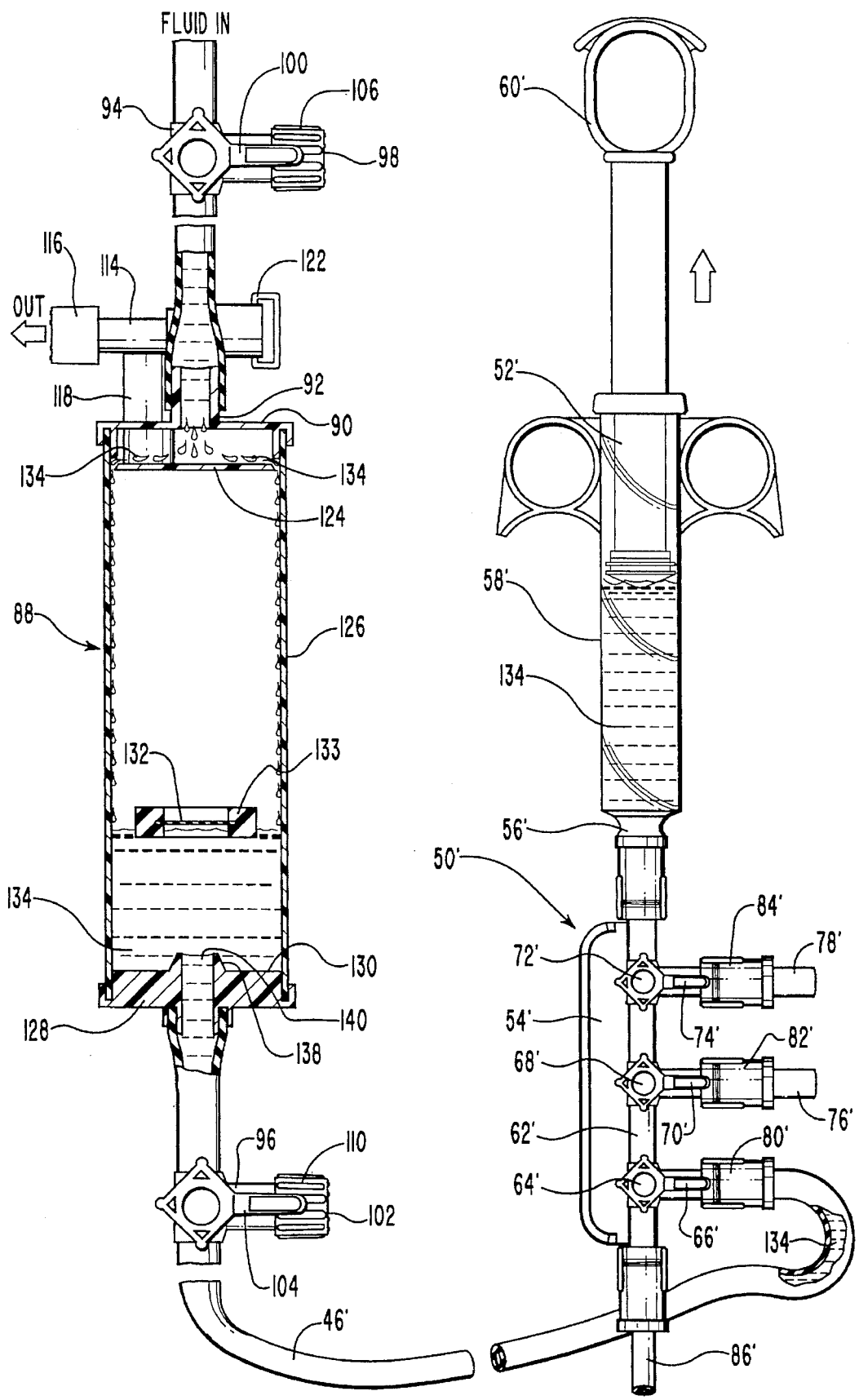

FIG. 6 shows the system in use during an intermediate phase of a procedure. A portion of outlet line 46' is shown in cross section so that it may be seen that there is fluid in outlet line 46'. In FIG. 6 fluid is being drawn into syringe 52' for a shot. As can be seen, contrast media is concurrently flowing into chamber barrel 126 to maintain the fluid level. Inlet handle 100 of inlet valve means 94 is turned toward inlet self vent 98 indicating that inlet line 26 is open. Outlet handle 104 of outlet valve means 96 is pointed toward outlet self vent 102 indicating that outlet line 46' is open at the point of outlet valve means 96. Outlet tab 66' of contrast media manifold valve 64' is turned toward syringe 52' indicating that manifold fluid line 62' is open at the point of contrast media manifold valve 64' also. Contrast media is thus able to flow through outlet line 46' into syringe 52'.

Figure 7:
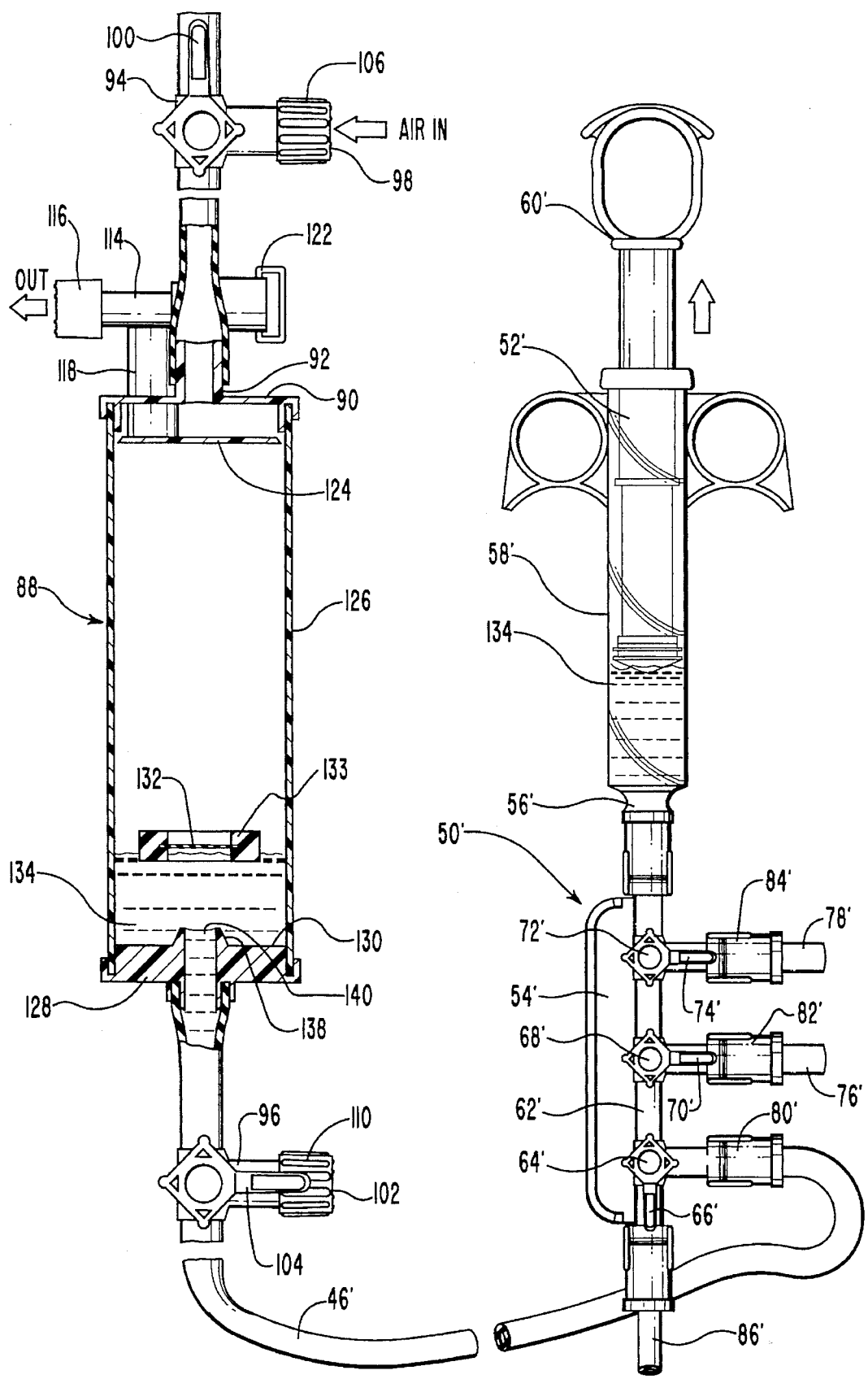

FIG. 7 illustrates the second to the last shot of a procedure. Here inlet handle 100 of inlet valve means 94 has been turned so that it is parallel to inlet line 26, which would be pointing in the direction of contrast media bag 12'. This indicates that inlet line 26' is occluded at the point of inlet valve means 94 while at the same time being vented to atmosphere at the point of inlet valve means 94. Air enters the system through inlet self vent 98.

In this stage, as fluid is drawn into syringe 52', chamber barrel 126 empties. Membrane 132 moves toward floor 136 where it will rest when substantially all of the fluid has been pulled from chamber barrel 126.

Outlet handle 104 of outlet valve means 96 is still turned to point toward outlet self vent 102 indicating that outlet line 46' is open at the point of outlet valve means 96. Tab 66' of contrast media manifold valve 64' points toward syringe 52' indicating that manifold fluid line 62' is open to allow fluid to flow to syringe 52' at the point of contrast media manifold valve 64'.

Figure 8:
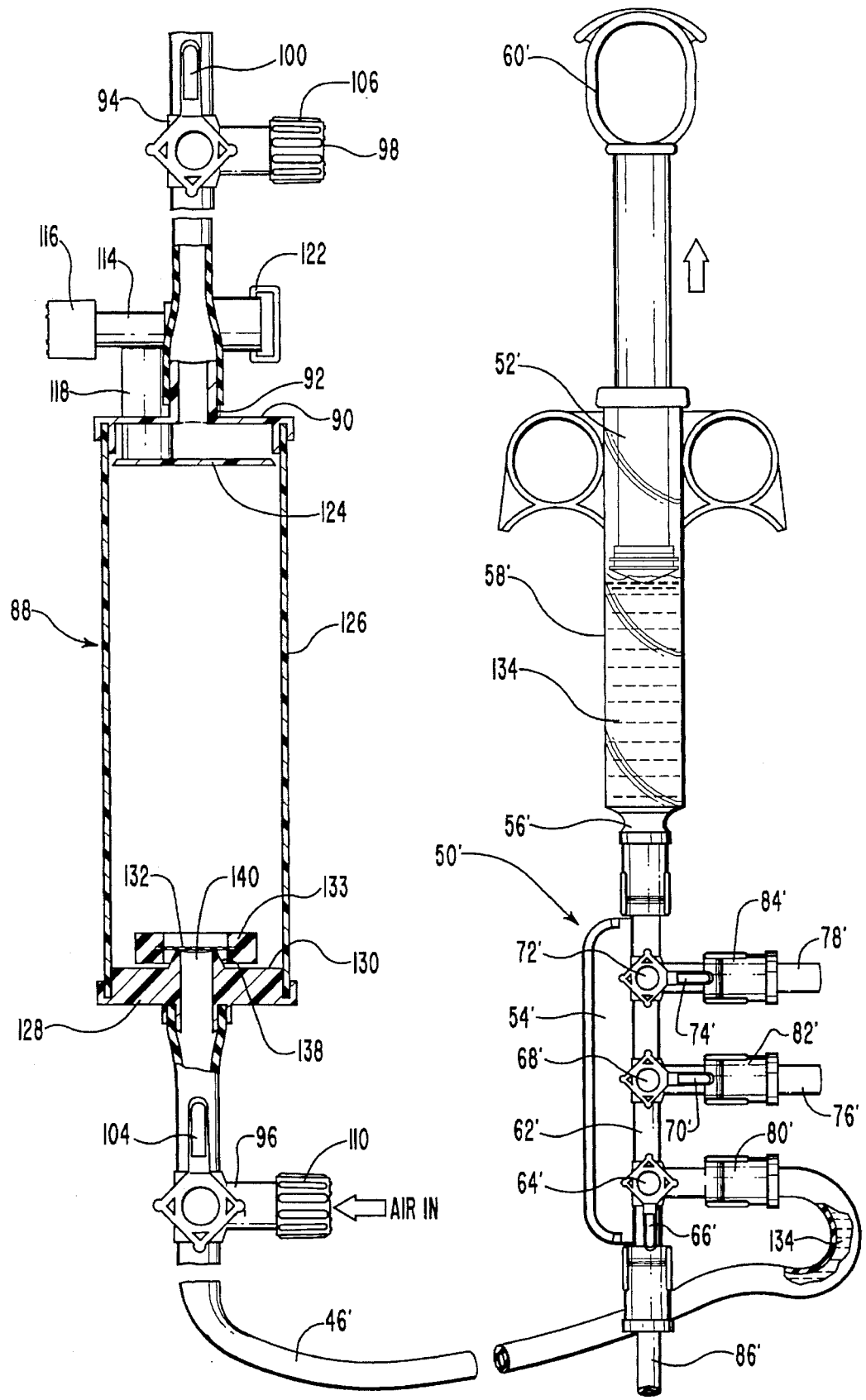

In FIG. 8 the last shot of a procedure is depicted. A portion of outlet line 46' is shown in cross section so that the presence of contrast media in outlet line 46' can be visualized. Here chamber barrel 126 is substantially emptied of contrast media. Membrane 132 has reached floor 136 and engaged nipple 138 to form a seal. Outlet handle 104 of outlet valve means 96 has been turned so that it points toward chamber means 88 indicating that outlet line 46' is occluded at the point or outlet valve means 96 while at the same time being vented to atmosphere at the point of outlet valve means 96 through self vent 102.

Here syringe 52' is being filled from the contrast media being pulled out of outlet line 46'. Typically outlet line 46' will be sized to hold nearly exactly one shot of contrast media. Plunger 60' can be pulled back relatively easily to fill syringe 52' with contrast media since outlet valve means 96 is providing venting for the system. The problems in overcoming the pressure differential and vacuum effect associated with an unvented system or in trying to vent the system by intervention of the medical user are eliminated.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system adapted for managing delivery of contrast media from a contrast media source to a manifold assembly which includes a syringe for injection from the manifold to a patient comprising:
   a. chamber means for receiving fluid from a contrast media source said chamber means having an inlet port at one end thereof and an outlet port at art opposite end thereof;
   b. an inlet line adapted for connection at one end thereof to a contrast media source, said inlet line connected at art opposite end thereof to said inlet port of said chamber means;
   c. an outlet line connected at one end thereof to said outlet port of said chamber means, said outlet line adapted for connection at an opposite end thereof to a manifold assembly; and
   d. a valve means disposed in said outlet line for controlling the flow of contrast media therethrough and comprising a means for venting to atmosphere, said valve means further comprising a handle means having a first position which permits flow of fluid through the line without venting to atmosphere, said handle means having a second position which permits fluid flow toward a patient while at the same time venting the system to atmosphere through said means for venting.

2. A contrast media delivery system as defined in claim 1 further comprising a deflector means disposed within said chamber means near said inlet port for routing fluid entering said chamber means down the sides of said chamber means.

3. A contrast media delivery system as defined in claim 2 further comprising a membrane and detent means disposed on an inner surface of said deflector means for preventing sealing engagement of said membrane with said deflector means.

4. A contrast media delivery system as defined in claim 1 further comprising a vent means for venting said chamber means and positioned thereon, said vent means having a first and second side, said first side having a button having first position and a second position thereby closing said vent when said button is in said first position and opening said vent when said button is in said second position, said second side having a filter which allows for venting therethrough.

5. A vent means as defined in claim 4 said vent means having a cage means attached thereto for preventing external occlusion of said vent.

6. A system adapted for managing delivery of contrast media from a contrast media source to a manifold assembly which includes a syringe for injection from the manifold to a patient comprising:
   a. chamber means for receiving fluid from a contrast media source said chamber means having an inlet port at one end thereof and an outlet port at an opposite end thereof;
   b. an inlet line adapted for connection at one end thereof to a contrast media source, said inlet line connected at an opposite end thereof to said inlet port of said chamber means;
   c. an outlet line connected at one end thereof to said outlet port of said chamber means, said outlet line adapted for connection at an opposite end thereof to a manifold assembly;
   d. a first valve means disposed in said inlet line for controlling the flow of contrast media therethrough and comprising a means for venting to atmosphere, said first valve means further comprising a handle means having a first position which permits flow of fluid through the line without venting to atmosphere, said handle means having a second position which permits fluid flow toward a patient while at the same time venting the system to atmosphere through said means for venting; and
   e. a second valve means disposed in said outlet line for providing alternative control of the flow of contrast media therethrough and comprising a means for venting to atmosphere, said second valve means further comprising a handle means having a first position which permits flow of fluid through the line without venting to atmosphere, said handle means having a second position which permits fluid flow toward a patient while at the same time venting the system to atmosphere through said means for venting.

7. A contrast media delivery system as defined in claim 6 further comprising a deflector means disposed within said chamber means near said inlet port for routing fluid entering said chamber means down the sides of said chamber means.

8. A contrast media delivery system as defined in claim 7 further comprising a membrane and detent means disposed on an inner surface of said deflector means for preventing sealing engagement of said membrane with said deflector means.

9. A contrast media delivery system as defined in claim 6 further comprising a vent means for venting said chamber means and positioned thereon, said vent means having a first and second side, said first side having a button having first position and a second position thereby closing said vent when said button is in said first position and opening said vent when said button is in said second position, said second side having a filter which allows for venting therethrough.

10. A vent means as defined in claim 9 said vent means having a cage means attached thereto for preventing external occlusion of said vent.

11. A system adapted for managing delivery of contrast media from a contrast media source to a manifold assembly which includes a syringe for injection from the manifold to a patient comprising:
   a. chamber means for receiving fluid from a contrast media source, said chamber means having an inlet port at one end thereof and an outlet port at an opposite end thereof;

b. an inlet line adapted for connection at one end thereof to a contrast media source, said inlet line connected at an opposite end thereof to said inlet port of said chamber means;

c. an outlet line connected at one end thereof to said outlet port of said chamber means, said outlet line adapted for correction at an opposite end thereof to a manifold assembly; and d. a valve means having a side port for venting to atmosphere, said valve means being disposed in said outlet line for controlling the flow of contrast media therethrough, said valve means further comprising a handle means having a first position which permits flow of fluid through the line without venting to atmosphere, said handle means having a second position which permits fluid flow toward a patient while at the same time venting the system to atmosphere through said side port.

12. A contrast media delivery system as defined in claim 11 further comprising a deflector means disposed within said chamber means near said inlet port for routing fluid entering said chamber means down the sides of said chamber means.

13. A contrast media delivery system as defined in claim 12 further comprising a membrane and detent means disposed on an inner surface of said deflector means for preventing sealing engagement of said membrane with said deflector means.

14. A contrast media delivery system as defined in claim 11 further comprising a vent means for venting said chamber means and positioned thereon, said vent means having a first and second side, said first side having a button having first position and a second position thereby closing said vent when said button is in said first position and opening said vent when said button is in said second position, said second side having a filter which allows for venting therethrough.

15. A vent means as defined in claim 14 said vent means having a cage means attached thereto for preventing external occlusion of said vent.

16. A system adapted for managing delivery of contrast media from a contrast media source to a manifold assembly which includes a syringe for injection from the manifold to a patient comprising:

a. chamber means for receiving fluid from a contrast media source said chamber means having an inlet port at one end thereof and an outlet port at an opposite end thereof;

b. an inlet line adapted for connection at one end thereof to a contrast media source, said inlet line connected at an opposite end thereof to said inlet port of said chamber means;

c. an outlet line connected at one end thereof to said outlet port of said chamber means, said outlet line adapted for correction at an opposite end thereof to a manifold assembly;

d. a first valve means having a side port for venting to atmosphere, said valve means being disposed in said inlet line for controlling the flow of contrast media therethrough, said first valve means further comprising a handle means having a first position which permits flow of fluid through the line without venting to atmosphere, said handle means a second position which permits fluid flow toward a patient while at the same time venting the system to atmosphere through said side port; and e. a second valve means having a side port for venting to atmosphere, said valve means being disposed in said outlet line for providing alternative control of the flow of contrast media therethrough, said second valve means further comprising a handle means having a first position which permits flow of fluid through the line without venting to atmosphere, said handle means having a second position which permits fluid flow toward a patient while at the same time venting the system to atmosphere through said side port.

17. A contrast media delivery system as defined in claim 16 further comprising a deflector means disposed within said chamber means near said inlet port for routing fluid entering said chamber means down the sides of said chamber means.

18. A contrast media delivery system as defined in claim 17 further comprising a membrane and detent means disposed on an inner surface of said deflector means for preventing sealing engagement of said membrane with said deflector means.

19. A contrast media delivery system as defined in claim 16 further comprising a vent means for venting said chamber means and positioned thereon, said vent means having a first and second side, said first side having a button having first position and a second position thereby closing said vent when said button is in said first position and opening said vent when said button is in said second position, said second side having a filter which allows for venting therethrough.

20. A vent means as defined in claim 19 said vent means having a cage means attached thereto for preventing external occlusion of said vent.

21. A system adapted for managing delivery of contrast media from a contrast media source to a manifold assembly which includes a syringe for injection from the manifold to a patient comprising:

a. chamber means for receiving fluid from a contrast media source said chamber means having an inlet port at one end thereof and an outlet port at an opposite end thereof, said chamber means further comprising:

i. a cylindrical body member having a first end with an interior portion and an exterior portion, and a second end with an interior portion and an exterior portion;

ii. a membrane slidably located within said cylindrical body member;

iii. an inlet port means for connecting to an inlet line positioned on said exterior portion of said first end;

iv. a vent means positioned on said exterior portion of said first end for venting said chamber means;

v. a deflection means positioned on said interior portion of said first end for deflecting fluid down a wall of said cylindrical body member as it enters said chamber means;

vi. a plurality of detents positioned on said interior portion of said first end whereby seating of said membrane in said first end is prevented;

vii. a nipple means positioned on said interior portion of said second end for ensuring said membrane seats with said interior portion of said second end thereby to prevent fluid flow; and viii. an outlet connection means positioned on said exterior portion of said second end for connecting to an inlet line;

b. an inlet line adapted for connection at one end thereof to a contrast media source, said inlet line connected at an opposite end thereof to said inlet port of said chamber means;

c. an outlet line connected at one end thereof to said outlet port of said chamber means, said outlet line adapted for connection at an opposite end thereof to a manifold assembly;

d. a first valve means having a side port for venting to atmosphere, said valve means being disposed in said inlet line for controlling the flow of contrast media therethrough, said first valve means further comprising a handle means having a first position which permits flow of fluid through the line without venting to atmosphere, said handle means having a second position which permits fluid flow toward a patient while at the same time venting the system to atmosphere through said side port; and e. a second valve means having a side port for venting to atmosphere, said valve means being disposed in said outlet line for providing alternative control of the flow of contrast media therethrough, said second valve means further comprising a handle means having a first position which permits flow of fluid through the line without venting to atmosphere, said handle means having a second position which permits fluid flow toward a patient while at the same time venting the system to atmosphere through said side port.

* * * * *

UNITED STATES PATENT AND TRADEMARK OFFICE
CERTIFICATE OF CORRECTION

PATENT NO. : 5,569,208
DATED : October 29, 1996
INVENTOR(S) : William R. Woelpper, et al.

It is certified that error appears in the above-indentified patent and that said Letters Patent is hereby corrected as shown below:

5,328,463 7/1994, "Bartone" should be -- Barton --
Column 1, line 20, "deliver" should be -- delivery --
Column 4, line 53, "pan" should be -- part --
Column 4, line 60, "tier" should be -- for --
Column 9, line 33, "art" should be -- an --
Column 9, line 37, "art" should be -- an --
Column 11, line 9, "correction" should be -- connection --
Column 11, line 46, "source said" should be -- source, said --
Column 11, line 56, "correction" should be -- connection --
Column 12, line 36, "source said" should be -- source, said --

Signed and Sealed this

Sixteenth Day of September, 1997

Attest:

BRUCE LEHMAN

*Attesting Officer*      *Commissioner of Patents and Trademarks*